(12) United States Patent
Gerlitz

(10) Patent No.: US 8,903,466 B2
(45) Date of Patent: *Dec. 2, 2014

(54) APPARATUS AND METHOD FOR NON-INVASIVE MEASUREMENT OF A SUBSTANCE WITHIN A BODY

(71) Applicant: GlucoVista Inc., Fairfield, NJ (US)

(72) Inventor: Yonatan Gerlitz, Herzliya (IL)

(73) Assignee: GlucoVista Inc., Fairfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/841,911

(22) Filed: Mar. 15, 2013

(65) Prior Publication Data
US 2013/0231539 A1    Sep. 5, 2013

Related U.S. Application Data

(63) Continuation-in-part of application No. 12/607,903, filed on Oct. 28, 2009.

(51) Int. Cl.
| | |
|---|---|
| A61B 5/00 | (2006.01) |
| A61B 5/05 | (2006.01) |
| A61B 5/1455 | (2006.01) |
| A61B 5/145 | (2006.01) |

(52) U.S. Cl.
CPC .......... *A61B 5/1455* (2013.01); *A61B 5/14532* (2013.01); *A61B 2560/0252* (2013.01); *A61B 5/0086* (2013.01)
USPC ............ 600/310; 600/316; 600/323; 600/365

(58) Field of Classification Search
USPC .......... 600/310, 316, 322, 323, 340, 365, 549
See application file for complete search history.

(56) References Cited

U.S. PATENT DOCUMENTS

| | | | |
|---|---|---|---|
| 3,770,958 | A | 11/1973 | Krakow |
| 5,237,178 | A | 8/1993 | Rosenthal et al. |

(Continued)

FOREIGN PATENT DOCUMENTS

| | | |
|---|---|---|
| EP | 0160768 A1 | 11/1985 |
| EP | 1568309 A1 | 8/2005 |

OTHER PUBLICATIONS

International Search Report dated Nov. 2, 2009 for International Application No. PCT/US2009/037829; 3 pages; Publisher: Korean Intellectual Property Office.

(Continued)

*Primary Examiner* — Clayton E Laballe
*Assistant Examiner* — Minh Phan
(74) *Attorney, Agent, or Firm* — Parsons Behle & Latimer

(57) ABSTRACT

A system for non-invasive measurement of a substance, such as glucose, includes a detector configured to sense radiation and an optical subsystem configured to focus the radiation on a sensitive area of the detector. The system includes one or more temperature sensors attached to one or more of a plurality of elements of the optical subsystem and to the detector and two or more temperature sensors configured to measure two or more respective ambient temperatures. The one or more temperature sensors are configured to measure the temperature of the one or more elements of the optical subsystem and the temperature of the detector. A method of measuring a concentration includes detecting an infrared radiation value, measuring the temperature of the detector, one or more components of the optical system, and two or more ambient temperatures, and correlating the temperatures with calibration parameters to correct the detected infrared radiation value.

20 Claims, 6 Drawing Sheets

(56) References Cited

U.S. PATENT DOCUMENTS

| | | | |
|---|---|---|---|
| 5,313,941 | A | 5/1994 | Braig et al. |
| 5,370,114 | A | 12/1994 | Wong et al. |
| 5,515,847 | A | 5/1996 | Braig et al. |
| 5,601,079 | A | 2/1997 | Wong et al. |
| 5,615,672 | A | 4/1997 | Braig et al. |
| 5,666,956 | A | 9/1997 | Buchert |
| 5,895,918 | A | 4/1999 | Powell et al. |
| 5,900,632 | A | 5/1999 | Sterling et al. |
| 6,198,949 | B1 | 3/2001 | Braig et al. |
| 6,647,350 | B1 | 11/2003 | Palfenier et al. |
| 6,949,070 | B2 | 9/2005 | Ishler |
| 6,998,247 | B2 | 2/2006 | Monfre et al. |
| 7,183,102 | B2 | 2/2007 | Monfre et al. |
| 7,254,427 | B2 * | 8/2007 | Cho et al. ................ 600/316 |
| 7,308,293 | B2 | 12/2007 | Gerlitz |
| 2002/0016533 | A1 | 2/2002 | Marchitto et al. |
| 2004/0257557 | A1 | 12/2004 | Block |
| 2005/0033186 | A1 | 2/2005 | Nordstrom et al. |
| 2005/0043630 | A1 | 2/2005 | Buchert |
| 2007/0106139 | A1 | 5/2007 | Nagata et al. |
| 2007/0197885 | A1 | 8/2007 | Mah et al. |
| 2008/0269580 | A1 | 10/2008 | Balistreri et al. |
| 2009/0259407 | A1 | 10/2009 | Gerlitz |

OTHER PUBLICATIONS

International Written Opinion dated Nov. 2, 2009 for International Application No. PCT/US2009/037829; 3 pages; Publisher: Korean Intellectual Property Office.

US Patent and Trademark Office; Final Office Action for US Application No. 112/607,903 dated Apr. 30, 2013.

US Patent and Trademark Office; Non-Final Office Action for U.S. Appl. No. 12/607,903 dated Nov. 27, 2012.

US Patent and Trademark Office; Non-Final Office Action for U.S. Appl. No. 12/607,903 dated Jun. 6, 2012.

International Search Report dated Mar. 23, 2011 from PCT/US2010/050901 filed Sep. 30, 2010.

International Search Report and Written Opinion of International Application PCT/US2010/050901 dated Mar. 23, 2011.

International Search Report for PCT/US 11/51218 Dated Jan. 26, 2012.

US Patent and Trademark Office, Office Action for U.S. Appl. No. 12/883,063, filed Sep. 15, 2010.

Office Action dated Apr. 4, 2014 issued in U.S. Appl. No. 12/883,063.

Canadian Intellectual Property Office dated May 22, 2014, issued in CA Patent Application No. 2,779,382.

* cited by examiner

APPARATUS AND METHOD FOR NON-INVASIVE MEASUREMENT OF A SUBSTANCE WITHIN A BODY

RELATED APPLICATION DATA

The present application is a continuation-in-part of U.S. application Ser. No. 12/607,903, filed Oct. 28, 2009, entitled APPARATUS AND METHOD FOR NON-INVASIVE MEASUREMENT OF A SUBSTANCE WITHIN A BODY, which is herein incorporated by reference.

BACKGROUND

The present application relates generally to the non-invasive measurement of various substances in a body, such as the measurement of the concentration of glucose in the human body and, more specifically, to a infrared detection system to analyze and determine, non-invasively, the concentration of a substance in a body.

Spectroscopic techniques using infrared ("IR") radiation are known in the prior art and have been widely used for non-invasive measurement of the concentration of substances of interest in a body. One area of particular interest is the use of these techniques for the non-invasive measurement of the concentration of glucose and other constituents of the human bloodstream.

The infrared spectra includes the near infrared (approximately 1 to 3 microns), the middle infrared (approximately 3 to 6 microns), the far infrared (approximately 6 to 15 microns), and the extreme infrared (approximately 15 to 100 microns). Known prior art glucose and other non-invasive blood constituent measuring devices operate in the near infrared regions where the absorption of infrared energy by glucose and other blood constituents is relatively low. However, it is known that glucose and other blood constituents have strong and distinguishable absorption spectra in both the middle and far infrared regions.

It has been found in a far infrared detection system that the resolution of the system should be equivalent to 0.01° C. to provide sufficiently accurate measurements. At this high level of accuracy, the blackbody emission of any component of the system (mirrors, filters, field limiters, detector, for example) can cause perturbations in the measurement. The known solution to such a circumstance is to cool the system to a cryogenic temperature (−180° C., for example), and have the system sealed and filled with dry nitrogen to avoid moisture accumulation. However, for a consumer product, such a solution is impractical and expensive.

SUMMARY

The present application discloses a system to measure, non-invasively, the concentration of a substance in a body. In accordance with one embodiment, an apparatus for the non-invasive measurement of a substance within a body includes a detector for sensing radiation emitted or remitted from a body, a human body, for example. An optical system is provided and aligned to focus IR radiation emitted by the body on a sensitive area of the detector.

Elements of the system within the field of view of the detector and the detector itself may have a temperature measuring device such as a thermistor attached to it for the purpose of measuring its temperature. At least two additional temperature measuring devices may measure two or more respective ambient temperatures, for example, an exterior ambient temperature and an interior ambient temperature. For the detector to accurately measure the energy radiated by the body, the system is calibrated to compensate for the effect of the temperature of individual elements in the detector field of view. Using a heating or heating/cooling unit for an individual element separately, the temperature of the element can be varied for the purpose of calibration while the temperatures of the other elements of the system remain stable. This process is repeated many times in various ambient temperatures and various body temperatures in order to calibrate the effect of an individual element on the measurement in all ranges of conditions relevant for the measurement.

This procedure is repeated for individual elements in the field of view of the detector yielding a look-up table ("LUT") representing the contribution of individual elements to the detector's measurement. The perturbations due to the temperature of individual system elements are taken into account in measurements, thereby enabling the system to obtain a high level of accuracy.

During the creation and build-up of the LUT, it was found that the temperature effect of a baffle used to limit the field of view of the detector is 10:1 relative to the body reading. Calibration alone cannot compensate for such a significant effect.

The solution is to reduce the emissivity of the baffle by enhancing its reflectivity. However, enhancing the reflectivity of the baffle creates an additional circumstance of reflecting stray energy to the detector. A spherical baffle was designed with an internal surface, i.e., the surface of the baffle opposite the detector, that is polished and gold-plated to lower the emissivity. The baffle design reduces reflection or multiple reflections from reaching the sensitive area of the detector.

The base plate that the detector and the baffle are mounted on and the baffle have substantially the same temperature as the detector. The base plate and the outer surface of the baffle are designed as a radiation trap having a dull black surface providing an emissivity of about 97%.

The design of the system optics creates an image of the detector sensitive area on the surface of the body in order to collect the IR radiation emitted or remitted from the body. The detector averages the IR radiation emitted or remitted from the area on the surface of the body subtended by the image of the detector.

In accordance with another embodiment, the present optical apparatus comprises two changeable optical filters, a first mirror positioned to a first side of the optical filter, and a second mirror positioned to a second side of the optical filter opposite the first mirror. A detector is positioned to the second side of the optical filter. A baffle partially surrounds a sensitive surface of the detector. Temperature-measuring devices are configured to measure the temperature of the baffle, mirrors and filters. The first mirror is configured to receive IR radiation from a measured surface of the body, collimate the IR radiation to a beam, and reflect the collimated IR beam toward and through the optical filter. One of the optical filters is configured to filter out a portion of the collimated IR beam having wavelengths that fall outside a selected bandwidth, and the second optical filter is configured to filter out a portion of the collimated IR beam having wavelengths that fall within a selected bandwidth. The filters are changeable by a motorized mechanism, and IR radiation measurements may include at least one measurement with one filter and a second measurement with the second filter. The second mirror is configured to receive the collimated and filtered IR beam and reflect it toward the detector. The baffle is configured to block stray IR radiation so that it does not reach the detector sensitive area.

The two radiation measurements are then corrected individually to reduce the effect of the emission of the system elements on the measurement. The ratio of the two radiation measurements after the correction and normalization for a black body reading is correlated to the concentration of the desired substance in the body, such as the concentration of glucose in the bloodstream of a human body, for example.

BRIEF DESCRIPTION OF THE DRAWINGS

The following figures, in which like numerals indicate elements, form part of the present specification and are included to further demonstrate certain features. The methods and apparatuses may be better understood by reference to one or more of these figures in combination with the detailed written description of specific embodiments presented herein.

These and other embodiments of the present application will be discussed more fully in the description. The features, functions, and benefits can be achieved independently in various embodiments, or may be combined in yet other embodiments.

DETAILED DESCRIPTION

One or more illustrative embodiments are described below. Not all features of an actual implementation are necessarily described or shown for the sake of clarity.

Figure 1:
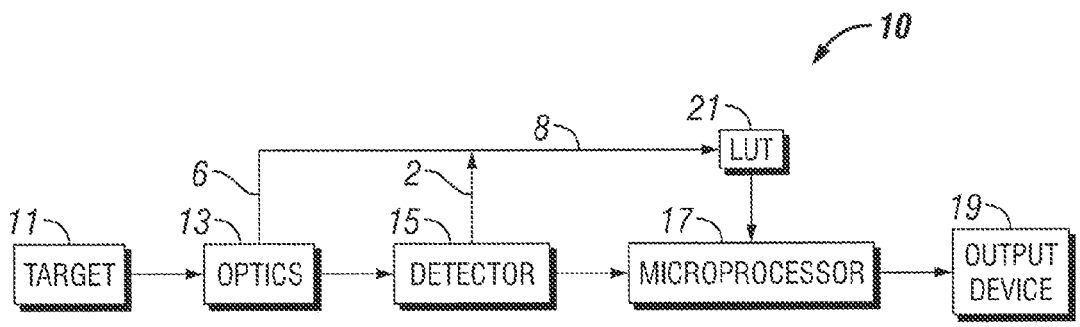
FIG. 1 illustrates a block diagram of a system for the non-invasive measurement of the concentration of a substance in a body.

Referring now to FIG. 1, a block diagram of a system 10 for the non-invasive measurement of the concentration of a substance in a body is shown. Infrared ("IR") radiation emitted or reflected from the surface of a body 11 is collected and collimated by optics subsystem 13 and focused on IR detector assembly 15. The body 11 is the source of the IR radiation being measured by the system 10. The body 11 is often a portion of a surface of a body of interest, such as a human body, for example. The optical subsystem 13 includes at least two changeable filters 33, 35, as shown in FIG. 2, that allow two different wavelength bandwidth signals, the first including a characteristic wavelength of a desired substance, such as glucose, for example, to be measured, the second being a portion of the emitted radiation not including the substance characteristic wavelength to be used as a reference signal.

Figure 4:
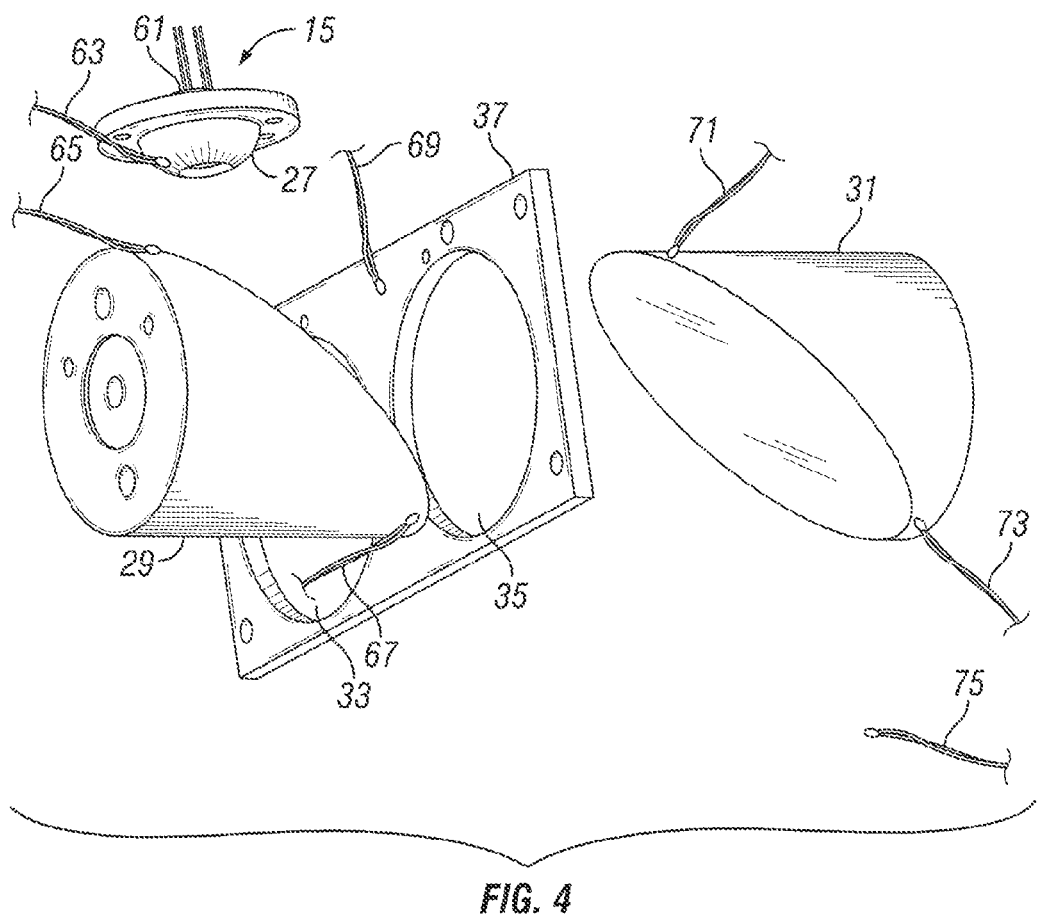
FIG. 4 is a perspective view of the optical and detector apparatus of FIG. 2, showing the locations on the various elements of the optical and detector apparatus of the temperature measurement devices.

The detector assembly 15 senses both signals and provides an output voltage that is proportional to the intensity of each of the two signal measurements to the microprocessor 17. Temperature sensors, as shown in FIG. 4, provide the temperatures of the various optical subsystem and detector assembly components and the ambient temperature to the microprocessor 17 via lines 2, 6, and 8 and a look up table ("LUT") 21. In a calibration process, the temperature of the optical subsystem and detector assembly individual components is varied while the temperature of the remaining system components is held stable to provide a set of calibration parameters that are stored in the LUT 21.

The microprocessor 17 uses the set of predetermined calibration parameters to correct each of the two radiation measurements to reduce the effect of the emission of the system elements on the measurement. The ratio of the two radiation measurements after the correction and normalization for a black body reading is correlated to the concentration of the desired substance in the body, such as the concentration of glucose in the bloodstream of a human body, for example. The result is then provided to an output device 19, such as an LCD or LED video monitor, for example.

Figure 2:
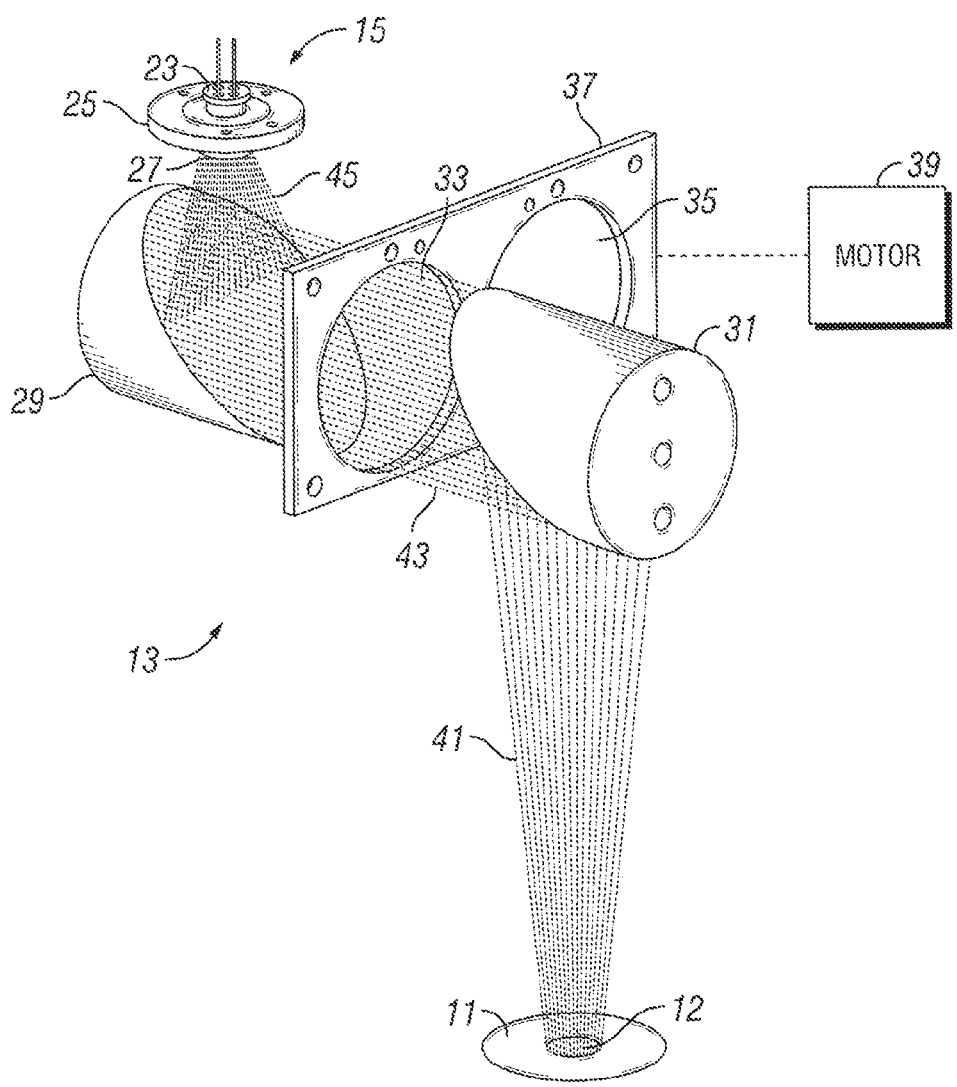
FIG. 2 is a perspective view of the optical and detector apparatus of FIG. 1 illustrating the path of travel for electromagnetic rays between the body and the detector.
Figure 3:
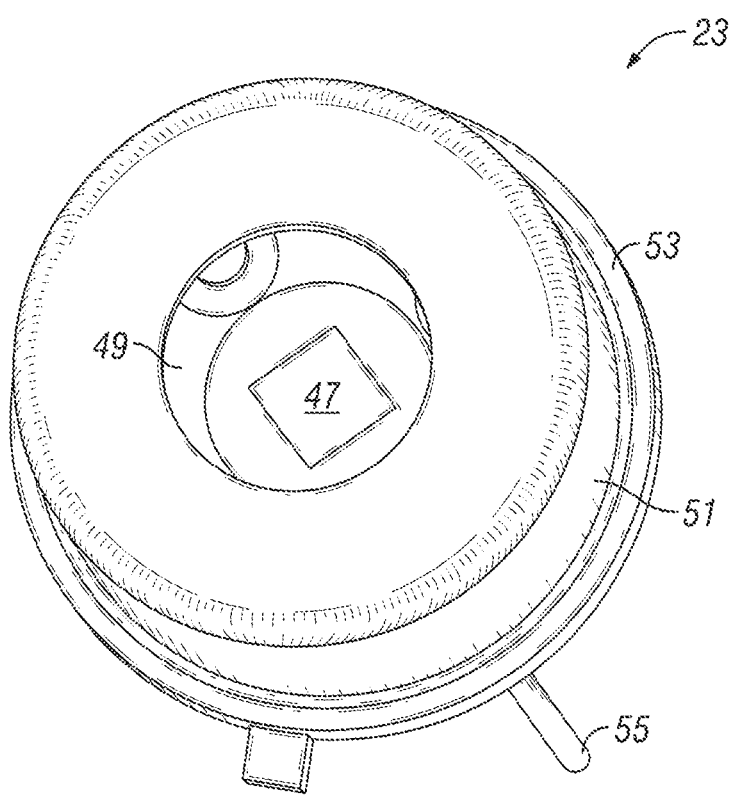
FIG. 3 is a perspective view of the detector of FIGS. 1 and 2.

Referring now also to FIG. 2, a schematic perspective view of the configuration of the optical and detector components of the system 10 shown in FIG. 1, illustrating the path of travel for IR rays between the body 11 and the detector 15 is shown. The detector 15 includes the detector element 23, detector base 25 and a baffle 27. The configuration of the optical and detector components is designed such that an image 12 of the sensitive or active area 47 of the detector 15 (as shown in FIG. 3) is created at the body 11 on the focal plane of mirror 31.

The area of image 12 may have a diameter approximately 6 mm. IR radiation emitted from or reflected by the body 11 at image 12 in beam 41 is collected and collimated by mirror 31. The IR radiation is reflected by mirror 31 and propagated to mirror 29 in a collimated beam 43 of parallel rays via filter 33 or filter 35. The focal plane of mirror 29 is located at the surface of the sensitive area 47 of the detector assembly 15. The beam 43 reaching mirror 29 is reflected and propagated as beam 45 and focused at the focal plane of mirror 29 incident on the detector assembly 15 sensitive area 47.

The detector assembly 15 is partially surrounded by a baffle 27 on the side facing the mirror 29. The baffle 27 insures that substantially only beam 45 is incident only on the sensitive area 47. Baffle 27 also blocks any stray radiation from reaching the sensitive area 47 of detector assembly 15. Thus, the optical subsystem 13 is aligned such that the image 12 is positioned at the surface of body 11 and the beam 41 of IR radiation is incident on the sensitive area 47 of detector assembly 15 via mirror 31, filter 33 or filter 35 and mirror 29.

In one embodiment, mirrors 29 and 31 are ninety-degree (90°) off-axis parabolic mirrors coated with gold or other suitable reflective material. Mirror 29 may have a focal length of about one (1) inch and mirror 31 may have a focal length of about three (3) inches. Other suitably designed reflective mirrors may be used for the optical subsystem 13 such as ellipsoid mirrors or a combination of ellipsoid and hyperbolic mirrors, for example.

Filter 33 and filter 35 are mounted in frame 37, frame 37 being positioned between mirror 29 and mirror 31. The filters 33, 35 are switched between positions intercepting the beam 43 using a suitable driving mechanism, such as a motor or pneumatic pressure, for example, coupled to frame 37. In one embodiment, motor 39 is coupled to the frame 37 and positions the frame 37 between the mirror 29 and mirror 31 such that the desired filter 33, 35 intercepts the beam 43. One of the filters, filter 33, for example, may be a narrow band filter passing the wavelengths of the spectral characteristic of the substance being measured. The other filter, filter 35, for example, may be a narrow band filter passing those wavelengths of a spectral characteristic not sensitive to the substance being measured. For example, in some embodiments, filter 33 may limit the bandwidth to that region of the spectrum where there is no emission for the substance being measured (for glucose, for example, the bandwidth would be 10.5μ-15μ), while filter 35 would have a bandwidth characteristic of the emission of the substance being measured (for glucose, the bandwidth would be 8.5μ-10.5μ).

Referring now also to FIG. 3, a perspective view of the detector element 23 shown in FIGS. 1 and 2 is illustrated. Any suitable IR detector responsive to the desired wavelengths of interest may be used. The detector element 23 includes a chip providing the IR sensitive material forming the detector sensitive area 47. The chip, or sensitive area 47, is enclosed in a case 51 and mounted to a base 53. The case 51 has an appropriately-sized opening forming a window 49 in its top surface to allow the IR radiation to reach the sensitive area 47. The window 49 is covered by a material transparent to the radiation of interest, such as silicon or other suitable material. Leads 55 connect the detector element 23 to the microprocessor 17 and other circuitry. In one embodiment, a passive IR sensor known as a thermopile detector is used. Thermopile detectors respond to IR power emitted by an object in its field of view by producing a voltage that is proportional to incident power. One suitable thermopile detector is manufactured by Dexter Research Corporation (part number ST150). The thermopile detector used in one embodiment has a sensitive area 47 with dimensions of 1.5 mm×1.5 mm and a window 49 of silicon.

Referring now also to FIG. 4, a perspective view of the optical subsystem 13 and detector assembly 15 of FIG. 2 is shown, illustrating suitable locations on the various elements of the optical subsystem and detector assembly where temperature measurement devices may be located. An individual element of the optical subsystem or detector assembly may emit electromagnetic radiation including IR radiation as a function of its temperature. In order to achieve the resolution used to produce an accurate measurement of the desired substance, the emission of individual elements in the system may be taken into account.

Elements of the optical subsystem 13 within the field of view of the detector assembly 15, as well as the detector assembly 15, include one or more suitable temperature sensing devices mounted at suitable locations on the element to accurately measure the temperature of the element. In one embodiment, thermistors are used as the temperature measuring devices. A thermistor is a temperature dependent resistor often composed of a semiconductor material. The resistance of a thermistor is inversely proportional to temperature, i.e., as the temperature increases, its resistance decreases. While other suitable temperature sensors can be used, thermocouples, for example, often a thermistor provides a greater output voltage.

In the embodiment shown in FIG. 4, thermistor 61 is located internally to the detector assembly 15 to measure the temperature of the cold junction where a thermopile detector is used. Thermistor 63 measures the temperature of the baffle 27. Thermistors 65 and 67 measure the temperature of mirror 29, and thermistors 71 and 73 measure the temperature of mirror 31. Two thermistors are used for each mirror due to the size and mass of the mirrors. Thermistor 69 measures the temperature of the filters 33, 35 and of frame 37 assembly. Thermistor 75 measures the ambient room temperature. The temperature of an individual element is matched with a set of predetermined calibration parameters stored in LUT 21 together with the temperature of detector 15, ambient temperature, and the temperature of body 11, to compensate for any perturbations in a substance concentration measurement due to the temperatures of the various optical subsystem and detector assembly elements.

Figure 7:
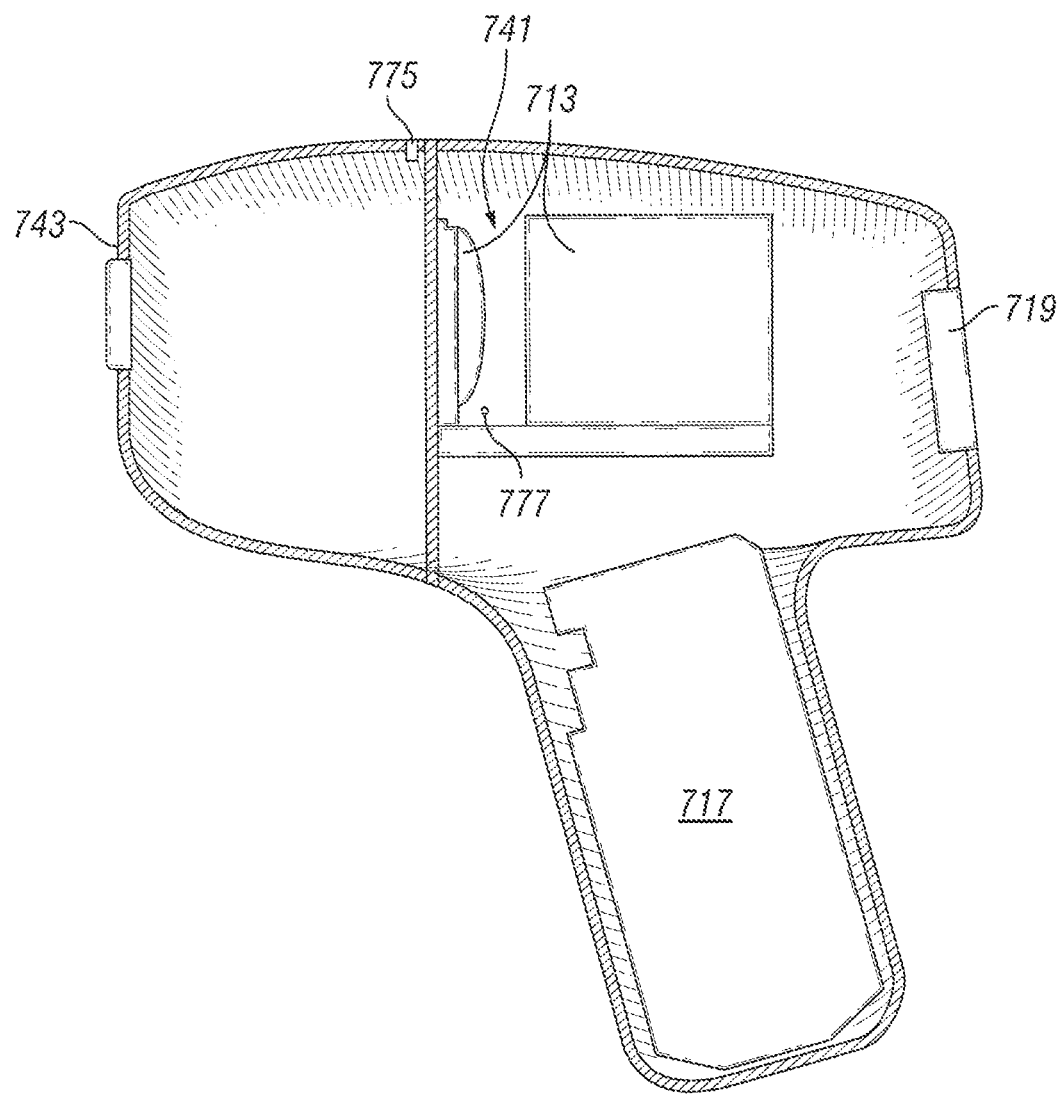
FIG. 7 is a cross-sectional view of another system for the non-invasive measurement of the concentration of a substance in a body showing the position of two thermistors measuring two ambient temperatures.

FIG. 7 is a cross-sectional view of a housing 743 containing a detector (not shown) that may be like detector 15 described herein and optical subsystem 713 that may be like optical subsystem 13 described herein. Housing 743 also contains a microprocessor 717 that may be like microprocessor 13 described herein and an output device 719 that may be like output device 19 described herein. An optical chamber 741 within housing 743 contains at least a portion of optical subsystem 713. A thermistor 777 measures an interior ambient temperature in optical chamber 741. The interior ambient temperature may be used to calculate directly the effect of the interior ambient temperature on the substance concentration measurement. Instead, or in addition, the interior ambient temperature may be used to calculate the effect of the interior ambient temperature on elements of optical subsystem 713 in accordance with their thermal capacity. Then, the effect of individual element temperature on the substance concentration measurement may be calculated. A thermistor 775 is mounted in an exterior facing cavity of housing 743 sealed from the interior of housing 743 and measures an exterior ambient temperature outside housing 743. Thermistor 775 may be used with a lookup table to calculate the effect of the exterior ambient temperature on a temperature of the measured surface. Thermistor 775 measures exterior ambient temperature at a point as close as possible to the measured surface without being so close as to be influenced by heat transfer from the measured surface itself.

Figure 5:
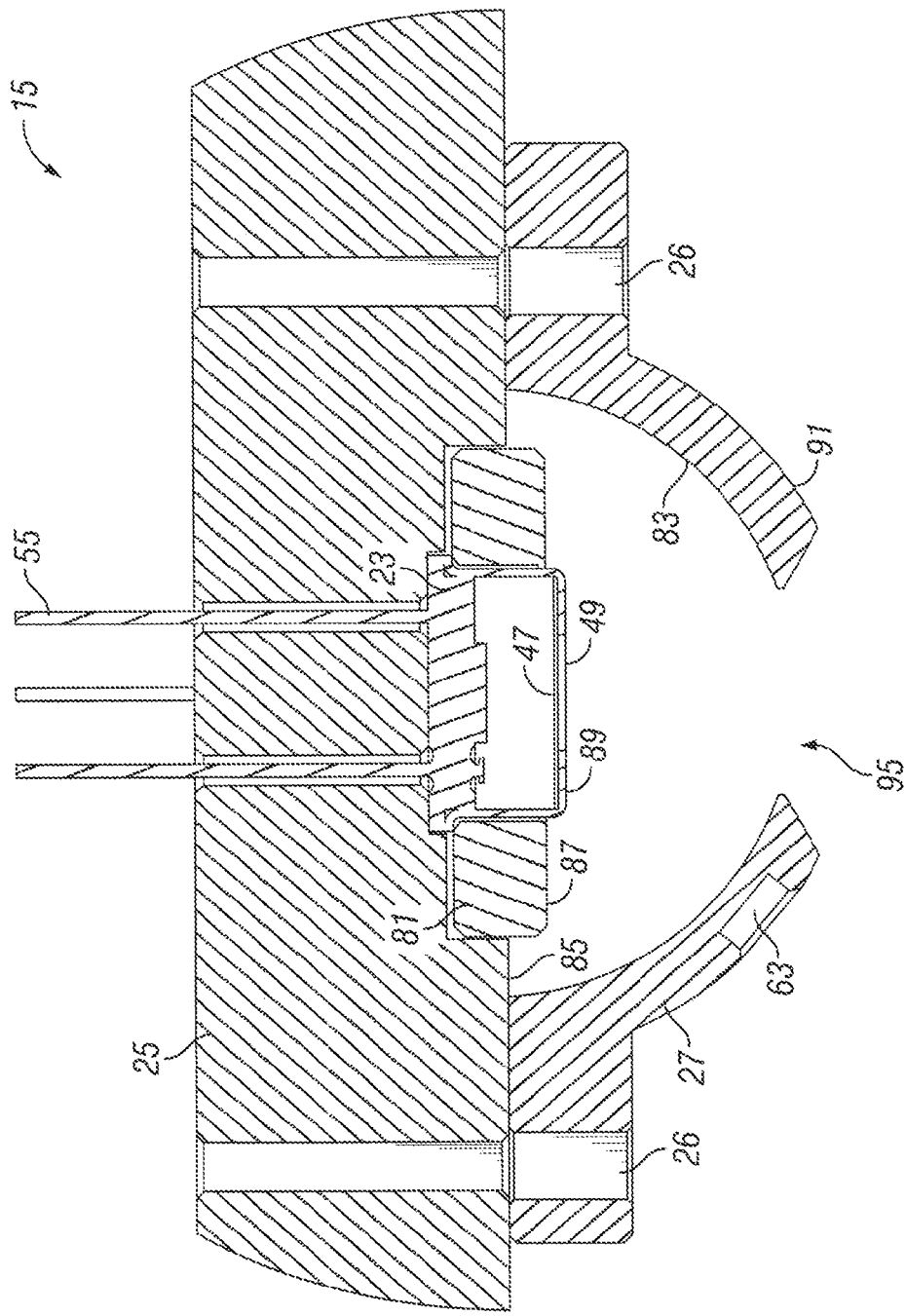
FIGS. 5 and 6 are cross-sectional views of the detector and baffle of the optical and detector apparatus shown in FIG. 2.

Referring now also to FIG. 5, a cross-sectional view of the detector assembly 15 and baffle 27 of the optical and detector apparatus of FIG. 2 is shown. In the illustrated embodiment, detector element 23 is held by a retainer ring 81 in thermal contact with detector base 25. Baffle 27 is attached to the detector base 25 with fasteners 26, establishing good thermal contact between the detector element 23, ring 81, detector base 25, and baffle 27. The inner surface 83 of baffle 27 may be gold-coated and polished to create a mirror. The inner surface 83 of baffle 27 is designed to have a very low emissivity and high reflectivity. The shape of the inner surface 83 of baffle 27 is designed to reduce reflection or multi-reflection of radiation incident on the sensitive area 47 of the detector element 23.

In one embodiment, the inner surface 83 of baffle 27 forms a spherical surface, the center of the sphere coinciding with the center of the detector sensitive area 47, enclosing the detector element 23. An opening 95 is formed in the portion of the sphere over and opposite the sensitive area 47. The dimensions of the opening 95 are sufficient to allow the beam 45 (as shown in FIG. 2) to be incident on the sensitive area 47 and reduce stray radiation reaching the detector sensitive area 47. The front surface 89 of the detector element 23, the exposed surface 87 of retainer ring 81 and the exposed portion 85 of detector base 25 within the sphere are coated with a suitable material, such as a suitable black coating, for example, to create a radiation trap for any stray radiation. Thermistor 63 measures the temperature of the baffle 27 to enable compensation for its emission effects on the substance concentration measurements.

Figure 6:
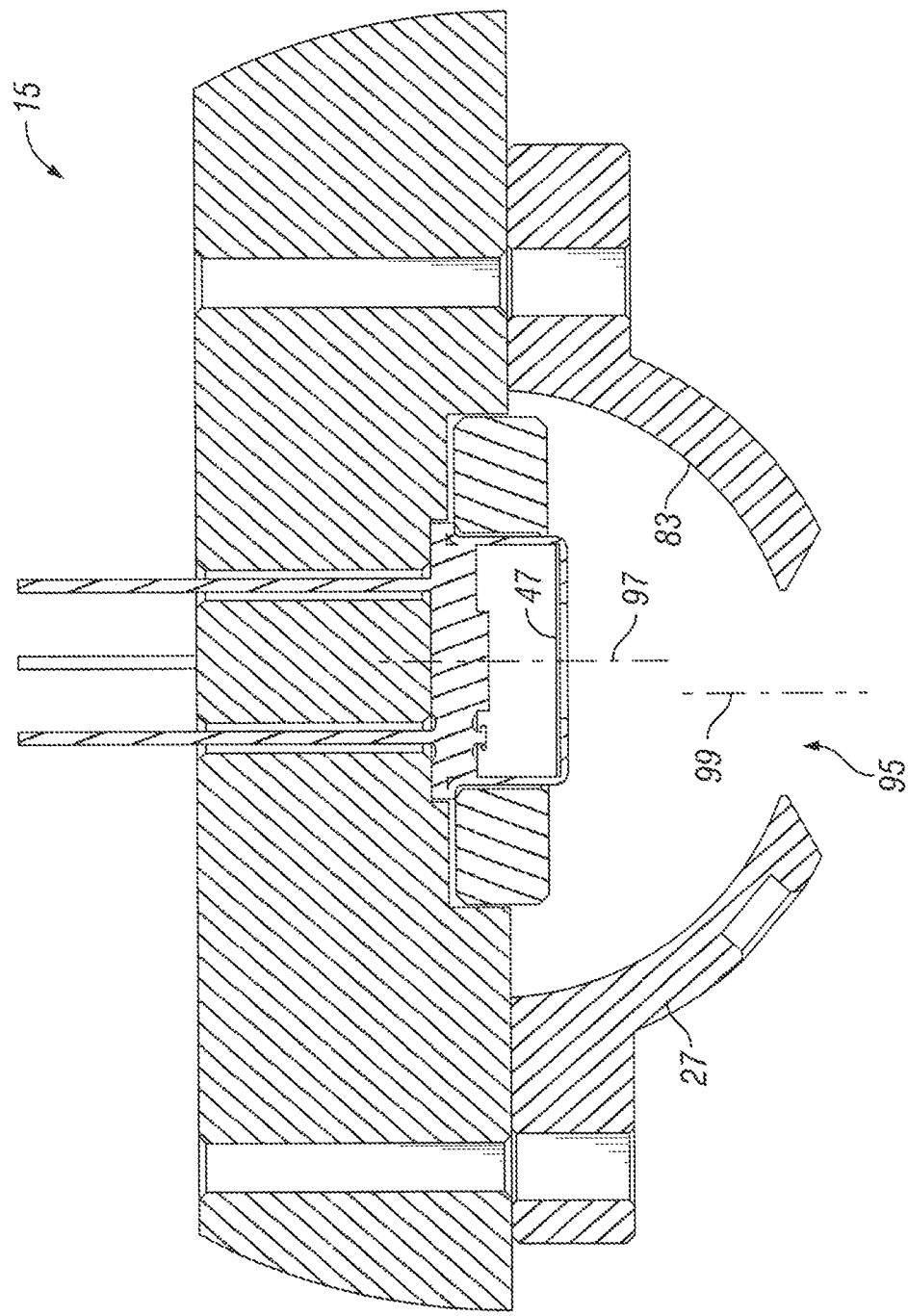

Referring now also to FIG. 6, a cross-sectional view of the detector assembly 15 and baffle 27 of the optical and detector apparatus of FIG. 2 according to another embodiment is shown. In this embodiment, as described above with reference to FIG. 2, mirrors 29 and 31 may be ninety-degree (90°) off-axis parabolic mirrors coated with gold or other suitable reflective material. The inner surface 83 of baffle 27 may form a spherical surface having the center 99 of the sphere positioned off center with respect to the center 97 of the detector sensitive area 47. An opening 95 is formed in the portion of the sphere over and opposite the sensitive area 47. Since the maximum of the IR energy distribution of an off-axis mirror is off center, the position of the center 99 of the baffle opening 95 is also offset from the center 97 of the detector sensitive area 27 to provide increased IR energy collection. The dimensions of the opening 95 are sufficient to allow the beam 45 (as shown in FIG. 2) to be incident on the detector sensitive area 47 and reduce stray radiation reaching the detector sensitive area 47.

Although the methods and apparatuses have been described in terms of certain embodiments, other embodiments that are apparent to those of ordinary skill in the art, including embodiments which do not provide all of the features and benefits set forth herein, are also considered included.

What is claimed is:

1. A system for non-invasive measurement of a substance within a human body, comprising:
   a detector configured to sense radiation emitted or remitted from the human body;
   an optical subsystem configured to focus the radiation on a sensitive area of the detector;
   one or more temperature sensors attached to one or more of a plurality of elements of the optical subsystem and to the detector, the one or more temperature sensors being configured to measure the temperature of the one or more elements of the optical subsystem and the temperature of the detector; and
   a microprocessor configured to reference a look-up table to compensate for perturbations in a substance concentration measurement due to the temperatures of the one or more elements of the optical subsystem and the temperature of the detector.

2. The system of claim 1, further comprising two or more temperature sensors configured to measure two or more respective surrounding ambient temperatures, wherein the temperature of one or more of the plurality of optical subsystem elements and the temperature of the detector are matched with a set of predetermined compensation parameters stored in the look-up table for compensating for an effect on the non-invasive measurement of a concentration of the substance caused by the temperature of each of the one or more of the plurality of elements and the detector, the two or more surrounding ambient temperatures, and a temperature measured at a surface of the human body.

3. The system of claim 2, wherein the detector comprises an infrared energy sensor, one of the two or more surrounding ambient temperatures is an exterior surrounding ambient temperature, and another of the two or more surrounding ambient temperatures is an interior surrounding ambient temperature.

4. The system of claim 2, wherein one of the two or more surrounding temperature sensors is mounted in an exterior facing cavity of a housing containing the detector and the optical subsystem and another of the two or more surrounding temperature sensors is mounted in an optical chamber inside the housing.

5. The system of claim 1, wherein the optical subsystem comprises one or more mirrors configured to focus the radiation on the sensitive area of the detector.

6. The system of claim 5, wherein the optical subsystem comprises at least two ninety degree (90°) off-axis parabolic mirrors.

7. The system of claim 5, wherein the optical subsystem comprises at least two mirrors including at least one attenuation filter disposed between the two mirrors for attenuating radiation in a selected wavelength band.

8. The system of claim 5 wherein the optical subsystem comprises two attenuation filters mounted on a moveable frame disposed between the two mirrors.

9. The system of claim 8 wherein the two attenuation filters comprise a first bandpass filter for attenuating radiation in a first selected wavelength band, the first selected wavelength band including at least one wavelength characteristic of the substance and a second bandpass filter for attenuating radiation in a second selected wavelength band, the second selected wavelength band reducing wavelengths characteristic of the substance.

10. Apparatus for non-invasive measurement of a substance within a body, the apparatus comprising:
    a detector for sensing radiation emitted or remitted from the body;
    optics configured to focus the radiation on a sensitive area of the detector;
    a baffle attached to and in thermal contact with the detector, the baffle being disposed to at least partially surround a detector sensitive area and configured to reduce the incidence of stray radiation on the detector sensitive area, wherein an interior surface of the baffle opposite the detector has a high reflectivity and low emissivity, the interior surface of the baffle being formed to reduce the incidence of radiation reflection or multi-reflection on the detector sensitive area;
    two or more temperature sensors configured to measure two or more respective ambient temperatures surrounding the apparatus, the detector, the optics, the baffle, or combinations thereof, the apparatus being configured to use the two or more surrounding ambient temperatures in measurement of the substance within the body; and
    one or more temperature sensors attached to one or more of a plurality of elements of the optics and to the detector, the one or more temperature sensors being configured to measure the temperature of the one or more elements of the optics and the temperature of the detector, wherein the temperature of the one or more of the plurality of optics elements and the temperature of the detector are matched with a set of predetermined compensation parameters stored in a look-up table for compensating for an effect on the non-invasive measurement of a concentration of the substance caused by the temperature of each of the one or more of the plurality of optics elements and the detector, the two or more surrounding ambient temperatures, and a temperature measured at a surface of the body.

11. The apparatus of claim 10, wherein the interior surface of the baffle constitutes a portion of a sphere surrounding the detector, a portion of the baffle above and opposite the sensitive area of the detector having an opening allowing the radiation to reach the sensitive area of the detector.

12. The apparatus of claim 11, wherein an exterior surface of the baffle being coated with a suitable black coating for absorbing stray radiation.

13. A method comprising:
    using an apparatus including a detector and an optical system;
    detecting an infrared radiation value emitted by a human body in a wavelength range including at least one wavelength characteristic of a substance in the human body;
    measuring the temperature of the detector and one or more components of the optical system;
    correlating the temperatures of the detector and the one or more components of the optical system with a set of predetermined calibration parameters to correct the detected infrared radiation value for the effects of the emission of each of the detector and the one or more components of the optical system; and noninvasively measuring a concentration of the substance in the human body.

14. A method as in claim 13, further comprising measuring two or more surrounding ambient temperatures and including the two or more surrounding ambient temperatures in the correlation of the temperatures of the detector and the one or more components of the optical system, wherein one of the two or more surrounding ambient temperatures is an exterior surrounding ambient temperature and another of the two or more surrounding ambient temperatures is an interior surrounding ambient temperature.

15. A method as in claim 14, wherein the exterior surrounding ambient temperature is measured in an exterior facing cavity of a housing containing the detector and the optical subsystem and the interior surrounding ambient temperature is measured in an optical chamber inside the housing.

16. A method as in claim 13, furthering comprising the step of limiting the wavelength range of the detected infrared radiation value.

17. A method as in claim 16, further comprising the step of limiting the wavelength range of the detected infrared radiation value to a first wavelength range including at least one wavelength characteristic of the substance to provide a first detected radiation value, and limiting the wavelength range of the detected infrared radiation value to a second wavelength range wherein wavelengths characteristic of the substance are reduced to provide a second detected radiation value.

18. A method as in claim 17, wherein the first wavelength range comprises $8.5\mu$ to $10.0\mu$ and the second wavelength range comprises $10.5\mu$ to $15.0\mu$ and the substance measured is glucose.

19. A method as in claim 17, further comprising the steps of:

correcting the first and second detected radiation values for the effects of the emission of each of the detector and the one or more components of the optical system;

normalizing the first and second detected radiation values for a blackbody reading; and correlating the ratio of the first and second detected radiation values to the concentration of the substance in the human body.

20. A method as in claim 13, further comprising referencing a look-up table and compensating for perturbations in the substance concentration measurement due to the temperatures of the one or more components of the optical subsystem and the temperature of the detector.

* * * * *